United States Patent
Echt et al.

(10) Patent No.: US 7,050,849 B2
(45) Date of Patent: May 23, 2006

(54) VIBRATIONAL THERAPY DEVICE USED FOR RESYNCHRONIZATION PACING IN A TREATMENT FOR HEART FAILURE

(75) Inventors: Debra S. Echt, Woodside, CA (US); Axel F. Brisken, Fremont, CA (US); Richard E. Riley, Palo Alto, CA (US); Mark W. Cowan, Fremont, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 6 days.

(21) Appl. No.: 10/869,705

(22) Filed: Jun. 15, 2004

(65) Prior Publication Data
US 2005/0131468 A1 Jun. 16, 2005

Related U.S. Application Data

(60) Provisional application No. 60/528,940, filed on Dec. 10, 2003, provisional application No. 60/518,138, filed on Nov. 6, 2003.

(51) Int. Cl.
*A61N 1/362* (2006.01)

(52) U.S. Cl. .................. 607/3; 607/9; 601/46
(58) Field of Classification Search .................. 607/2, 607/3, 4, 5, 119, 122, 129; 601/46
See application file for complete search history.

(56) References Cited

U.S. PATENT DOCUMENTS

| | | | |
|---|---|---|---|
| 3,857,382 A | 12/1974 | Williams et al. | |
| 4,265,228 A * | 5/1981 | Zoll | ............................ 601/108 |
| 4,651,716 A | 3/1987 | Forester et al. | |
| 5,018,523 A | 5/1991 | Bach, Jr. et al. | |
| 5,174,289 A | 12/1992 | Cohen | |
| 5,935,158 A * | 8/1999 | Holmstrom et al. | ........ 607/116 |
| 6,070,101 A | 5/2000 | Struble et al. | |
| 6,223,079 B1 | 4/2001 | Bakels et al. | |
| 6,408,205 B1 * | 6/2002 | Renirie et al. | .................. 607/5 |
| 6,439,236 B1 | 8/2002 | Porter et al. | |
| RE38,119 E | 5/2003 | Mower | |
| 2004/0015104 A1 * | 1/2004 | Goldberger | .................... 601/2 |

FOREIGN PATENT DOCUMENTS

| | | |
|---|---|---|
| WO | WO 99/061058 | 12/1999 |
| WO | WO 03/070323 | 8/2003 |

OTHER PUBLICATIONS

ACC/AHA Task Force on Practice Guidelines. Evaluation and Management of Chronic Heart Failure in the Adult. *JACC* 2002;38:2101-13.
Bradley DJ et al., "Cardiac Resynchronization and Death from Progressive Heart Failure: A Meta-Analysis of Randomized Controlled Trials," *JAMA* 2003;289:730-740.

(Continued)

*Primary Examiner*—Robert E. Pezzuto
*Assistant Examiner*—Tammie Heller
(74) *Attorney, Agent, or Firm*—Townsend and Townsend and Crew LLP

(57) ABSTRACT

Systems for pacing the heart include a vibrational transducer which directs energy at the heart, usually at at least a ventricle, to pace the heart and to promote synchronized contraction of the ventricles. Optionally, additional vibrational and/or electrical stimulation may be provided. The vibrational transducers are usually implantable at a location proximate the heart.

11 Claims, 6 Drawing Sheets

OTHER PUBLICATIONS

Daoud et al., "Implantation Techniques and Chronic Lead Parameters of Biventricular Pacing Dual-chamber Defibrillators", *J Cardiovasc Electrophysiology* 2002; 13:964-970.

Daubert et al., "Permanent Left Ventricular Pacing With Transvenous Leads Inserted Into The Coronary Veins", *PACE* 1998;21;239-245.

Daubert et al., "Use of Specifically Designed Coronary Sinus Leads for Permanent Left Ventricular Pacing: Preliminary Experience", *PACE*, 1997; 20: II-NASPE Abstract 17, Apr., 1997.

David Trial Investigators, "The Dual Chamber and VVI Implantable Defibrillator (DAVID) Trial," *JAMA* 2002;288:3115-3123.

Leclercq C et al., "Systolic Improvement and Mechanical Resynchronization does not Require Electrical Synchrony in the Dilated Failing Heart with Left Bundle-Branch Block", *Circulation* 2002;106:1760-1763.

Leclerq C et. al., "Acute Hemodynamic Effects of Biventricular DDD Pacing in Patients with End-Stage Heart Failure", *JACC* 1998;32:1825-1831.

Linde C et al., "Long-Term Benefits of Biventricular Pacing in Congestive Heart Failure: From the Multisite Stimulation in Cardiomyopathy (MUSTIC) Study", *J Am Coll Cardiol* 2002;40:111-118.

Miracle Trial Investigators, "Combined Cardiac Resynchronization and Implantable Cardioversion Defibrillation in Advanced Heart Failure: the Miracle ICD Trial," *JAMA* 2003;289:2685-2694.

Nielsen JC et al., "A Randomized Comparison of Atrial and Dual-Chambered Pacing in 177 Consecutive Patients with Sick Sinus Syndrome," *J Am Coll Cardiol* 2003;42:614-623.

Valls-Bertault et al., "Adverse Events with Transvenous Left Ventricular Pacing in Patients with Severe Heart Failure: Early Experience from a Single Centre", *Europace* 2001;3:60-63.

* cited by examiner

VIBRATIONAL THERAPY DEVICE USED FOR RESYNCHRONIZATION PACING IN A TREATMENT FOR HEART FAILURE

CROSS-REFERENCES TO RELATED APPLICATIONS

The present application claims priority from U.S. patent application Ser. No. 60/518,138, filed Nov. 6, 2003; and U.S. patent application Ser. No. 60/528,940, filed Dec. 10, 2003, the full disclosures of which are incorporated herein by reference.

The disclosure of the present application is also related to the following applications being filed on the same day as the present application: U.S. patent Ser. No. 10/869,776; U.S. patent application Ser. No. 10/869,242; and U.S. patent application Ser. No. 10/869,631, the full disclosures of which are incorporated herein by reference.

BACKGROUND OF THE INVENTION

1. Field of the Invention

The systems and methods of this invention relate to pacing treatment of the heart comprising applying vibrational energy.

Heart Failure (HF) currently affects over 5 million patients in the United States alone. This population has been steadily increasing due to overall demographic aging and, in particular, the effects of new life-prolonging treatments to patients with chronic cardiac conditions. HF is defined by ACC/AHA Task force as a complex clinical syndrome that impairs the ability of the ventricle to fill with or eject blood. New medications developed to treat HF have been generally ineffective, and device-based solutions appear to present a significant opportunity for afflicted patients.

HF generally results from one or more underlying factors including hypertension, diabetes, valvular disease, cardiomyopathy, coronary artery disease, or structural changes to the heart muscle. HF is characterized by reduced ventricular wall motion in systole and/or diastole, and low ejection fraction. As the heart becomes less able to pump sufficient volume to the system, patients develop symptoms of fluid retention, shortness of breath, and fatigue.

Approximately one third of patients with HF have poor timing of contraction between the right and the left ventricle and within the left ventricle, called interventricular and intraventricular dyssynchrony, respectively. This is sometimes also manifest by a wider than normal QRS interval on a surface electrocardiogram (ECG) taken of a HF patient. The wider than normal QRS interval is called conduction delay because there is a prolonged time interval for the normal electrical impulse to travel ("conduct") to all parts of both ventricles. This is also sometimes manifest by conduction delay between the atria and ventricles (A-V delay). Ventricular dyssynchrony and conduction delays can contribute to weak left ventricular function by causing delayed and/or abnormal left ventricular contraction. There may be inadequate filling and emptying of the left ventricle, as well as backflow of blood into the left atrium, resulting in decreased cardiac output and increased symptoms for the patient. This dysfunction causes increased mortality and morbidity among patients with HF.

Cardiac resynchronization therapy is the use of pacing to coordinate the contraction of the ventricles in order to reduce heart failure and improve prognosis in HF patients. Recently, devices that pace both ventricles, referred to as bi-ventricular pacing, have been adopted to provide cardiac resynchronization therapy. A bi-ventricular pacing system utilizes conventional dual chamber, right atrium and right ventricle, pacing technology but adds a third lead, usually in a coronary vein, to sense and pace the epicardial surface of the left ventricle. The pacing device can then, at an appropriate time interval after right atrial activity, synchronize contraction of both right and left ventricles either simultaneously or at coordinated time intervals. The synchronous contraction of the ventricles facilitates more adequate filling of the left ventricle and less backflow (mitral valve regurgitation to the left atrium), resulting in more oxygenated blood being pumped to the body. Alternatively, it has been shown that pacing only the left ventricle at a location near the apex is associated with improvement in left ventricular function. However, this location is not accessible from the coronary veins in current pacing systems.

Clinical studies have shown a sustained improvement of symptoms and exercise tolerance in patients using bi-ventricular pacing devices to improve left ventricular function. Cardiac resynchronization therapy has also been incorporated into implantable cardioverter defibrillator (ICD) devices, allowing for the simultaneous treatment of heart failure and the prevention of sudden cardiac death caused by life-threatening ventricular arrhythmias in HF patients.

Pacemaker leads are typically placed through the skin into a subclavian vein to access the venous side of the cardiovascular system. In bi-ventricular pacing systems, one lead is placed in contact with the right ventricular wall and one lead is placed in contact with the right atrial wall. To access the left ventricle, the third lead is passed into the right atrium, into the orifice of the coronary sinus, and then maneuvered through the coronary veins to a position on the epicardial aspect of the lateral wall of the left ventricle. Some work has been done exploring minimally invasive methods of alternatively placing the lead/electrode directly on the epicardium of the left ventricle.

Placement of the third lead to contact the left ventricle has been a significant problem for application of this therapy. The coronary sinus is a complicated venous pathway with multiple branches which bend and narrow with considerable variation as they extend distally onto the epicardium of the left ventricle. Placement of this lead requires significant skill on the part of the physician. In order to provide adequate steerability and pushability, the design of the left ventricular lead or a lead introduction system/device is much more complicated than for regular pacing leads. Often the left ventricular lead positioning/placement can take over an hour to perform exposing the patient to increased fluoroscopy radiation and increased procedure risks. Furthermore, in some patients (7.5% in the MIRACLE study), an acceptable lead placement is not possible due to anatomic constraints or undesirable phrenic nerve pacing. Additionally, lead dislodgement and loss of pacing capture have been a common complication in the use of these coronary sinus leads (e.g., 10–20% complication rates have been reported within the first 6 months of device placement).

It would be beneficial to eliminate the third pacing lead and yet provide resynchronization within the left ventricle and/or between the left and right ventricles. Moreover, it would be beneficial to provide more physiological pacing of the right ventricle. In normal physiology, the right ventricle is first stimulated in the upper septal area, and then the impulse travels down specially conducting pathways to the right ventricular apex. However, pacing from the right ventricle is virtually always accomplished from a lead tip located in the right ventricular apex, such that the conduction pathway is abnormal and slow. Clinical trials have recently shown that in patients with and without A-V block, pacing from the right ventricular apex can result in increased total mortality and re-hospitalization for heart failure compared to non-paced patients. The possible adverse effects of pacing the right ventricular apex in patients without bi-ventricular pacemakers is unknown, but a source of growing concern.

2. Description of the Background Art

This application has disclosure related to prior commonly assigned provisional applications 60/479,347, filed on Jun. 17, 2003; 60/496,184, filed on Aug. 18, 2003; 60/496,179, filed on Aug. 18, 2003; and 60/507,719, filed on Sep. 30, 2003. The full disclosures of each of these prior filings are incorporated herein by reference.

U.S. Pat. No. 4,928,688/RE38,119 Mower; Method and apparatus for treating hemodynamic dysfunction.

U.S. Pat. No. 5,174,289 Cohen: Pacing systems and methods for control of the ventricular activation sequence.

U.S. Pat. No. 5,018,523 Bach et al.; Apparatus for common mode stimulation with bipolar sensing.

U.S. Pat. No. 6,070,101 Struble et al.; Multiple channel, sequential, cardiac pacing systems.

U.S. Pat. No. 6,439,236 Porter and Xie; Methods of inducing atrial and ventricular rhythms using ultrasound and microbubbles.

PCT WO 03/070323 Adam et al; Ultrasound Cardiac Stimulator.

U.S. Pat. No. 6,223,079 Bakels et al.; Bi-ventricular pacing method.

U.S. Pat. No. 4,651,716 Forester et al.; Method and device for enhancement of cardiac contractility.

PCT WO 9961058 Van der Wouw; Method of altering heart beat.

ACC/AHA Task Force on Practice Guidelines. Evaluation and Management of Chronic Heart Failure in the Adult. *JACC* 2002;38:2101–13.

Daubert et al., "Use of Specifically Designed Coronary Sinus Leads for Permanent Left Ventricular Pacing: Preliminary Experience", PACE, 1997; 20: II-NASPE Abstract 17, April, 1997.

Leclerq C et. al., "Acute Hemodynamic Effects of Biventricular DDD Pacing in Patients with End-Stage Heart Failure", *JACC* 1998;32:1825–1831.

Daubert et al., "Permanent Left Ventricular Pacing With Transvenous Leads Inserted Into The Coronary Veins", *PACE* 1998;21;239–245.

Daoud et al., "Implantation Techniques and Chronic Lead Parameters of Biventricular Pacing Dual-chamber Defibrillators", *J Cardiovasc Electrophysiology* 2002; 13:964–970.

Valls-Bertault et al., "Adverse Events with Transvenous Left Ventricular Pacing in Patients with Severe Heart Failure: Early Experience from a Single Centre", *Europace* 2001; 3:60–63.

Leclercq C et al., "Systolic Improvement and Mechanical Resynchronization does not Require Electrical Synchrony in the Dilated Failing Heart with Left Bundle-Branch Block", *Circulation* 2002; 106:1760–1763.

Linde C et al., "Long-Term Benefits of Biventricular Pacing in Congestive Heart Failure: From the Multisite Stimulation In Cardiomyopathy (MUSTIC) Study", *J Am Coll Cardiol* 2002;40:111–118.

Abraham W T et al., "Cardiac Resynchronization in Chronic Heart Failure", *N Engl J Med* 2002;346: 1845–1853.

Bradley D J et al., "Cardiac Resynchronization and Death from Progressive Heart Failure: A Meta-Analysis of Randomized Controlled Trials," *JAMA* 2003;289:730–740.

Nielsen J C et al., "A Randomized Comparison of Atrial and Dual-Chambered Pacing in 177 Consecutive Patients with Sick Sinus Syndrome," *J Am Coll Cardiol* 2003;42: 614–623.

DAVID Trial Investigators, "The Dual Chamber and VVI Implantable Defibrillator (DAVID) Trial," *JAMA* 2002; 288:3115–3123.

MIRACLE Trial Investigators, "Combined Cardiac Resynchronization and Implantable Cardioversion Defibrillation in Advanced Heart Failure: the MIRACLE ICD Trial," *JAMA* 2003 ;289:2685–2694.

BRIEF SUMMARY OF THE INVENTION

For this invention, the use of a device to effect left ventricular pacing and/or to synchronize left ventricular pacing with right ventricular activation provides an improved method of treating patients with heart failure or possibly of preventing heart failure. The improvement uses vibrational energy to effect left ventricular pacing to the left ventricle without the use of an implanted intracardiac or epicardial lead in contact with the left ventricle. Optionally, a system and method of the present invention may rely on delivery of the vibrational energy from an external source to provide temporary left ventricular pacing treatment for heart failure. The system described is a fully implanted subcutaneous device that provides ultrasound energy at frequencies, amplitudes, and treatment durations that stimulate cardiac tissue without the use of leads contacting left ventricular tissue.

A treatment regime for providing synchronized beating of the left and right ventricle is accomplished in part by applying a vibrational energy wave. The vibrational wave stimulates the heart. Once stimulated, a QRS complex can be seen on an electrocardiogram and contraction of the heart chamber(s) is initiated. In this invention, the wave will either a) simultaneously stimulate both ventricles to contract, b) stimulate the ventricles in a preferred, more physiologic, conduction pattern, or c) be delivered in coordination with an electrical pacing and sensing lead, such that one ventricle is electrically paced and the vibrational wave stimulates the other ventricle. Vibrational energy offers the potential benefit of being able to stimulate without tissue contact, and, therefore, is not limited to the right ventricular apex as a pacing site nor does it require direct placement and contact of a lead in or on the left ventricle.

The vibrational wave can be applied to stimulate each heart beat with ultrasound as a single burst or as multiple bursts with appropriate selection of the following parameters:

| Parameter | Value Range |
| --- | --- |
| Ultrasound frequency | 20 KHz–5 MHz |
| Burst Length (#cycles) | 3–250 |
| Pace Pulse Duration | 0.12 µS–13 mS |
| Duty Cycle | 0.1–100% |
| Intensity | >0.2 W/cm$^2$ |

The device would contain one or more ultrasound transducers of appropriate size and aperture to stimulate heart tissue within the ultrasound beam. The transducer portion of the device would be implanted subcutaneously in the anterior chest surface of the body in such fashion as to target the desired heart tissue within the beam profile of the transducer. The beam profile would need only target a sufficient volume of tissue to generate a vibrationally-induced paced beat. If the tissue volume required for stimulation is small, a narrow beam could used. However, a wide beam could also be used and could successfully stimulate multiple chambers simultaneously. Furthermore, multiple beams could be utilized to stimulate multiple sites within the heart, either simultaneously or sequentially per a programmable delay function.

In a combined electrical pacing and vibrational pacing device, the synchronization of the delivery could be accomplished either within a single enclosure or in two separate enclosures. Separate enclosures would require communication between the devices to synchronize the beats or detection of an electrically-paced beat by one device and an immediate vibrationally-paced beat response by the other device, or vice-versa.

As in all pacemaker devices, which include a variety of pacing modalities, the delivery of the vibrational pacing energy could be triggered based on sensed or programmed heart rates or inhibited by sensed cardiac events in the atrium or ventricle. When used for bi-ventricular pacing, with vibrational pacing of the left ventricle in combination with electrical pacing of the right ventricle, the vibrational energy would be triggered to be synchronous, i.e. simultaneous or at a programmable delay, from the right ventricle electrically-paced beat. Fundamentally, if a right ventricular beat is triggered or sensed by the vibrational device, then vibrational energy is delivered to the left ventricle to synchronize the chambers.

In the simplest form, the device would contain a vibrational energy delivery mechanism to stimulate the left ventricle. It would provide a fixed programmable heart rate that stimulates a paced beat of the left ventricle via vibrational energy. The paced beat would then normally conduct to the right ventricle. This would be analogous to a ventricular pacing and sensing (with inhibition) referred to as a VVI pacing modality. An enhanced pacing modality referred to as VVI/T also includes programmability to trigger a paced beat in response to a sensed beat.

In a more complex form, the device would contain multiple vibrational energy mechanisms to stimulate the heart tissue at multiple points, e.g., at multiple locations within the left ventricle, and/or within both the left and right ventricles. Stimulation could occur either simultaneously, or sequentially per a programmable function.

In the most complex form, the device would contain a vibrational energy delivery mechanism for left ventricular stimulation and also contain electrical capabilities for pacing and sensing of both right atrial and right ventricular chambers with programmable capabilities for all combinations of pacing modalities (e.g. DDDR+, Dual chamber pacing, Dual chamber sensing, Dual chamber triggered and inhibited modes with Rate responsive sensors and mode adaptation). Optionally, the device would contain the capability for high energy delivery used for cardioversion and defibrillation, using either electrical energy or vibrational energy.

DETAILED DESCRIPTION OF THE INVENTION

Figure 1A:
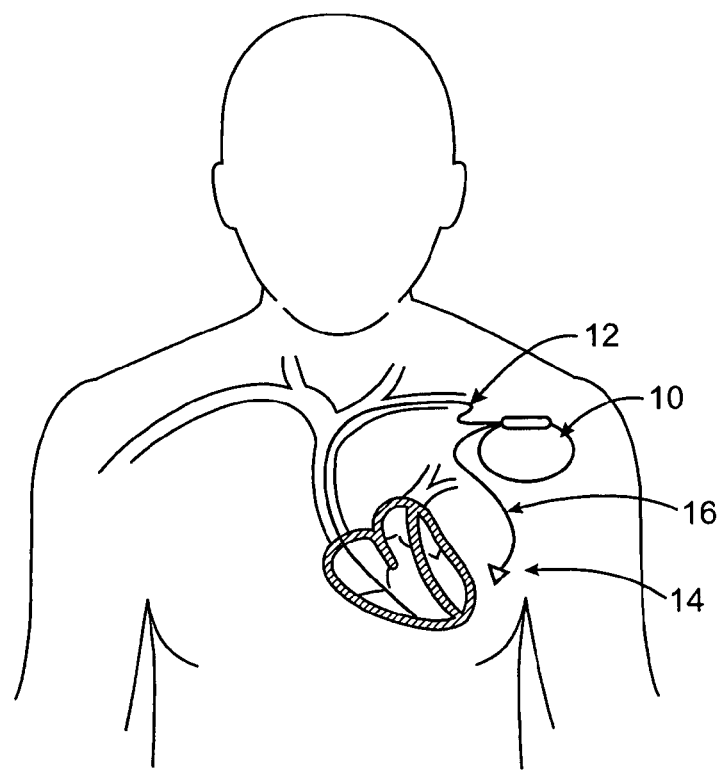
FIGS. 1A and 1B illustrate two embodiments with one or more right-sided transvenous leads; a left-sided transducer over or between the ribs with a left-sided canister implant (FIG. 1A), and a medial transducer placement over the sternum with a right-sided canister implant (FIG. 1B).
Figure 1B:
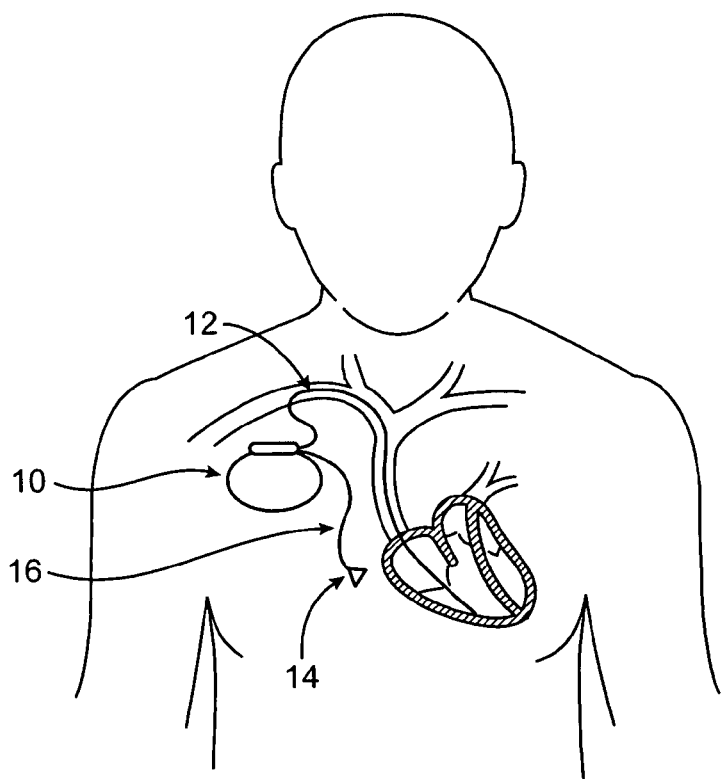

In one exemplary embodiment, all the device sensing, logic and energy source components are housed within a single canister 10 implanted beneath skin and adipose tissue in the left (FIG. 1A) or right (FIG. 1B) subclavian region of the chest wall. In this embodiment, electrical leads 12 containing electrodes are passed transvenously through the superior vena cava into the right atrium and/or right ventricle. An ultrasound transducer 14 is separately connected to the canister by a cable 16. The transducer is encased in an appropriate housing and is subcutaneously implanted over the ribs, over the sternum, or between the ribs in order to target the preferred region of the left or right ventricle within the ultrasound beam profile. The connecting cable 16 is tunneled subcutaneously to the canister and connected.

Alternatively, two canisters may be implanted subcutaneously beneath skin and adipose tissue (not shown). The first canister houses the device sensing, logic and energy source components required for the electrical pacemaker/cardioverter/defibrillator and may be implanted on the left or right subclavian regions. The second canister is located in the left anterior chest region over the ribs or between the ribs or it is located over the sternum. The second canister houses the transducer, device sensing, logic, and energy source for pacing using vibrational energy. A connecting cable is tunneled subcutaneously between the two canisters.

Figure 2A:
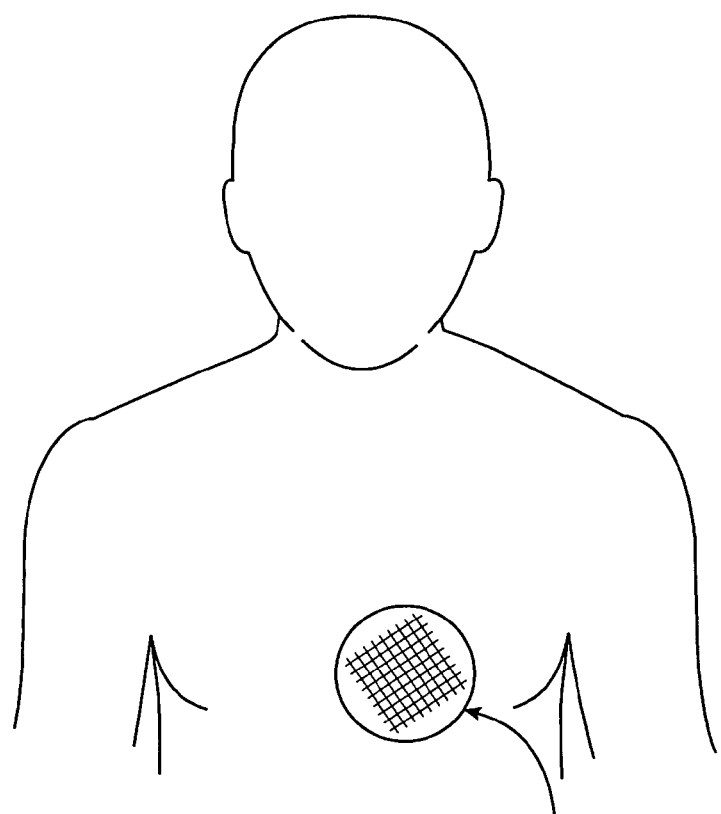
FIGS. 2A and 2B illustrate an alternative embodiment without leads and a canister housing the ultrasound transducer implanted in the left precordial subcutaneous space.
Figure 2B:
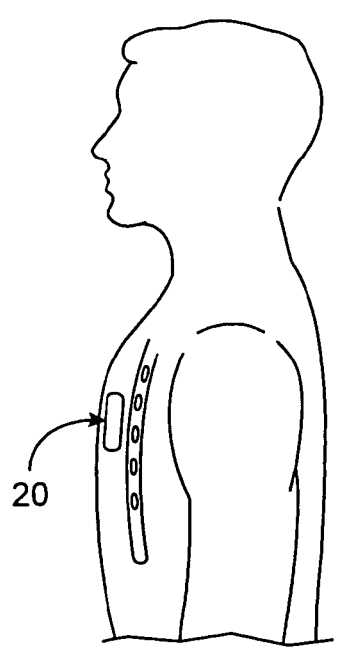

In another embodiment, (FIGS. 2A and 2B), the device 20 is a single canister with no transvenous leads. As previously disclosed the device can be subcutaneously implanted in the left anterior chest region or over the sternum with the ultrasound beam(s) directed to the ventricle(s) from a transducer within the canister. This represents a programmable rate VVI/T device that paces only the left ventricle or simultaneously or sequentially paces the left and right ventricles using vibrational energy. An electrocardiogram sensing circuit would preferably be provided in this embodiment with electrodes on the surface of the canister, and would provide either an inhibited pacing operation with a detected ventricular beat or a synchronized pacing operation with a detected ventricular beat.

Figure 3A:
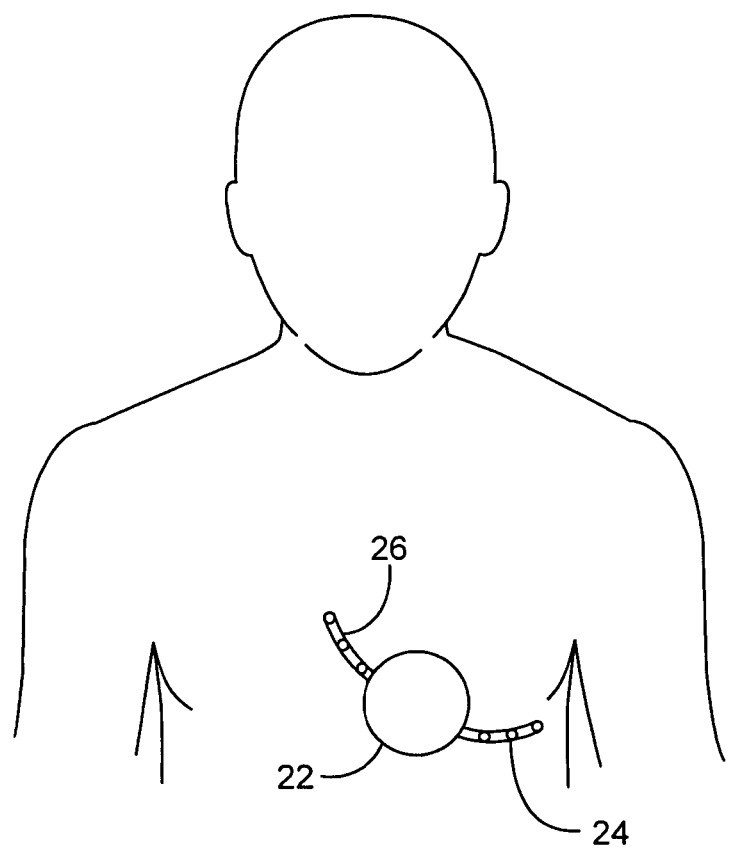
FIGS. 3A and 3B illustrate an alternative embodiment with one or more subcutaneous leads attached to a canister implanted in the left precordial subcutaneous space.
Figure 3B:
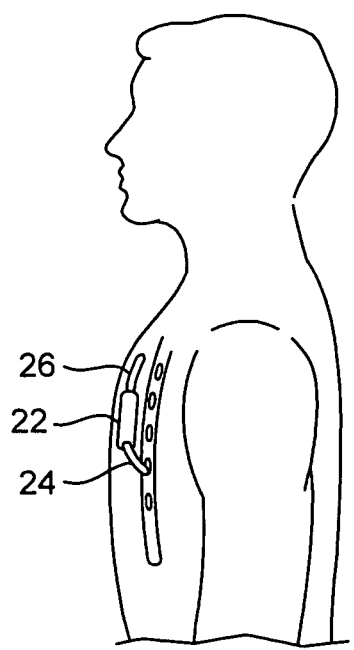

In another embodiment, (FIGS. 3A and 3B), the device 22 is a single canister housing the sensing, logic, and energy source components for pacing using vibrational energy. One or more subcutaneous leads 24 and 26 containing one or more vibrational energy elements arranged linearly or in another pattern are connected to device 22. Electrodes for sensing of the electrocardiogram (sensors) are provided on either or both leads 24 and 26 or the surface of the canister. This represents an alternative programmable rate VVI/T device that paces either the left ventricle or simultaneously or sequentially paces the left and right ventricles using vibrational energy.

In another embodiment (FIG. 4), the device 30 is a single canister with transvenous lead 32 containing capability for electrical sensing and pacing and transvenous lead 34 containing capability for electrical sensing and pacing and vibrational pacing. The single canister 30 would be implanted beneath skin and adipose tissue in the left or right subclavian region. In this embodiment, the right ventricular lead 34 (FIG. 5) containing both electrical and vibrational energy components, and a right atrial lead 32 containing electrical energy components are utilized. The leads are passed transvenously through the superior vena cava into the right ventricle and the right atrium. In this embodiment transducer(s) 36 would be contained within the body of the right ventricular lead. The transducer(s) 36 would deliver vibrational energy to pace one or both ventricles. The electrical component of the right ventricular lead would primarily be used for sensing, but could optionally be used for electrical pacing. The right atrial lead would be used for both sensing and pacing.

Figure 4:
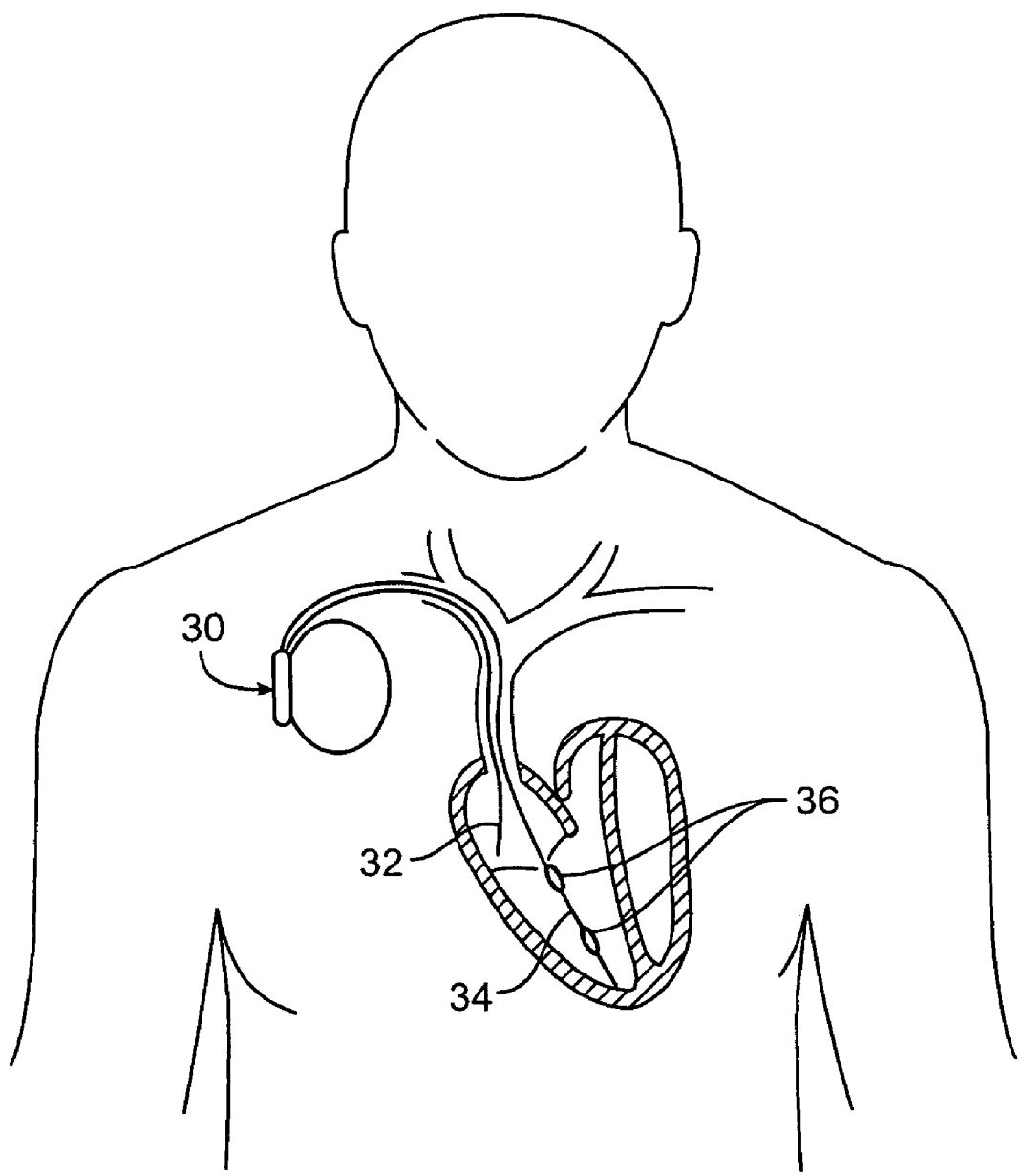
FIG. 4 illustrates an alternative embodiment with two right-sided transvenous leads, a ventricular lead incorporating a transducer within the lead body and an atrial lead, and a canister in the right subcutaneous space.
Figure 5:
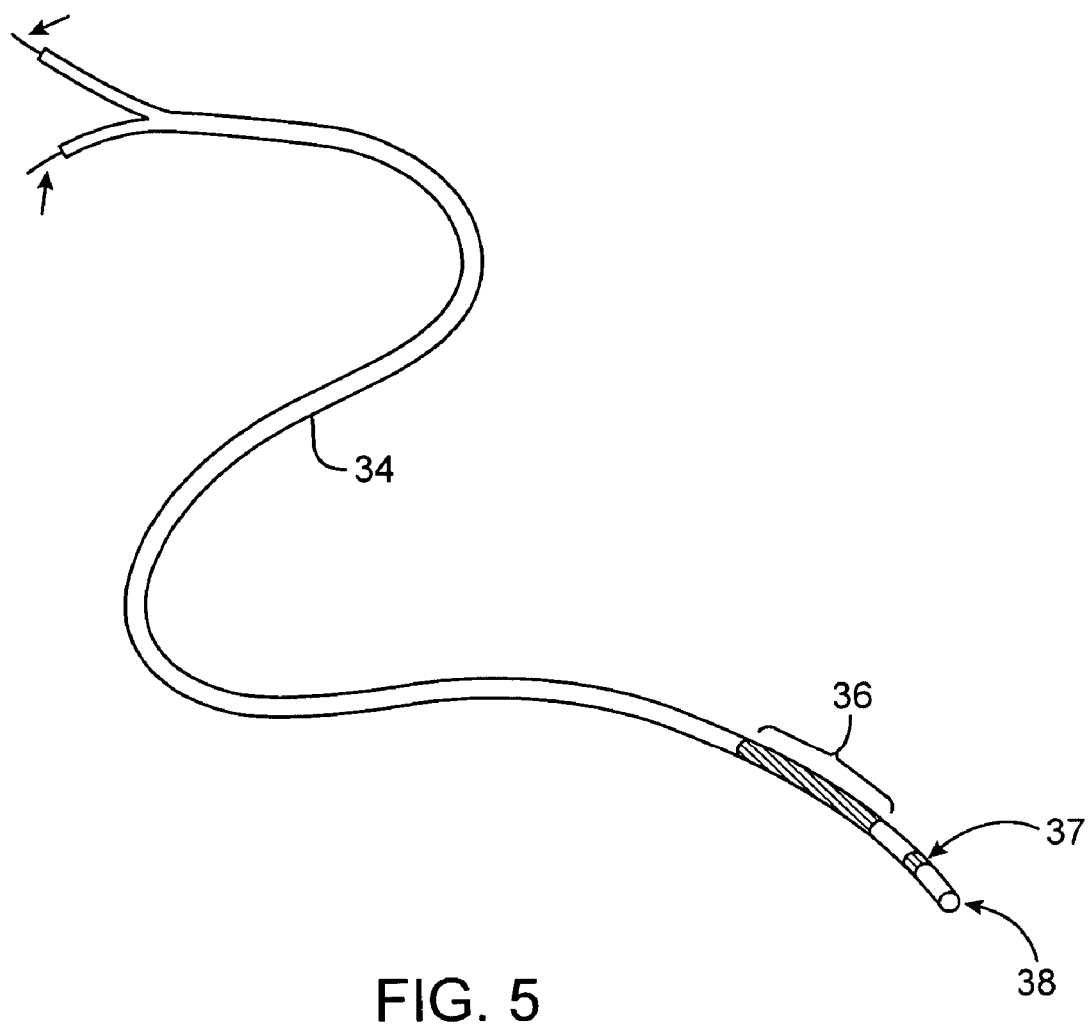
FIG. 5 illustrates a lead design incorporating an electrode pair at the distal end for pacing and sensing, and one or more transducers within the body of the lead.

Another embodiment would be similar to FIG. 4, except that both the right atrial lead 32 and right ventricular lead 34 would contain both electrical 37 and 38 and vibrational 36 energy components as shown in FIG. 5. In this embodiment, the right atrial lead would function in a manner similar to the right ventricular lead, to accomplish pacing and sensing of the right and left atria.

Alternatively, the right atrial lead 32 would not be present, and the right ventricular lead would be as shown in FIG. 5 with an added electrical sensing electrode (not shown) located on a proximal portion of the lead such that the electrode would be positioned within the right atrium.

Alternatively, the right atrial lead would not be present, and the right ventricular lead would be as shown in FIG. 5 with an added electrical sensing electrode (not shown) and with an added vibrational energy transducer (not shown) located on a proximal portion of the lead such that the components would be positioned within the right atrium. In this embodiment a single lead could provide pacing and sensing of the right and left atria and separately pacing and sensing of the right and left ventricles.

Figure 6:
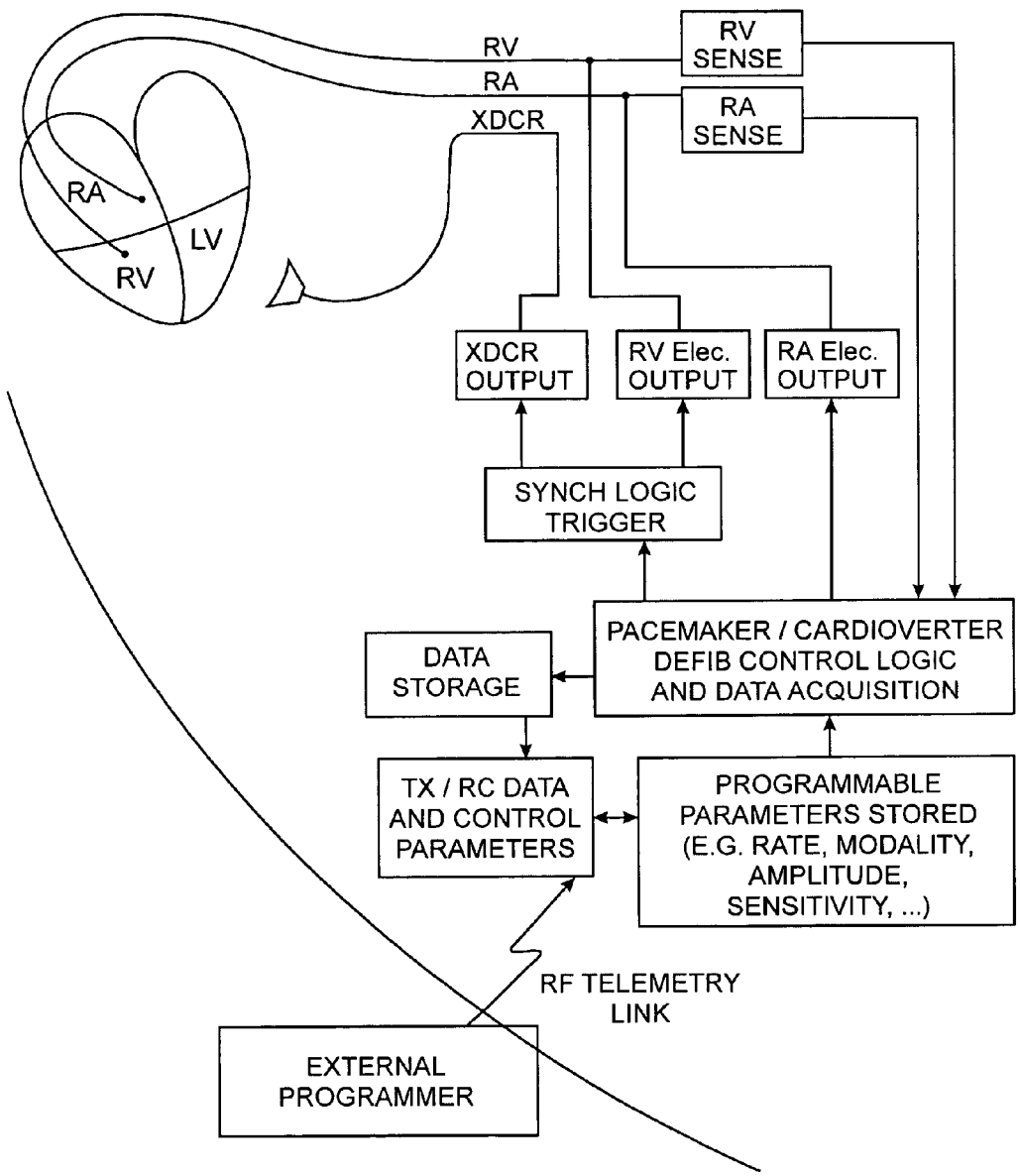
FIG. 6 is a block diagram showing an embodiment of the control circuitry implementation of the present invention.

FIG. 6 provides a block diagram of circuitry for implementing the most complex version of the device including dual chamber sensing, dual chamber electrical pacing, electrical cardioversion and defibrillation, and vibrational energy pacing. Alternatively, the cardioversion and defibrillation may be provided by vibrational energy.

The device designs and implementations referred to thus far are generally useful for the treatment of patients with heart failure. The treatment of heart failure, however, may be accomplished with systems which may be somewhat simpler that those described above to promote temporary synchronized contraction of the ventricles. In particular, the vibrational transducers may be adapted for manual control by either the patient or by a doctor or other medial personnel. Most simply, the vibrational transducer may be incorporated into external units capable of being applied to the anterior chest (not shown). Usually, the patient will be reclining on the table or bed, the vibrational transducer, attached by a cable to an external generator, is applied over the patient's chest, preferably using a gel layer to enhance contact. Usually, the transducer will be placed generally over the ventricular region of the heart and the transducer may be configured to direct energy over specific ventricular regions.

Systems embodied for external use have sensor circuitry, control circuitry, power supply, and burst generation incorporated into the generator (not shown). The ECG sensors may be incorporated into the transducer housing or optionally standard transcutaneous electrodes may be connected to the body and to the generator via cables. Alternatively, the generator may accept ECG signals directly from an external electrocardiogram system. Intrinsic heart signals detected from ECG sensors are analyzed by control circuitry and are used to control pacing using the vibrational energy as discussed above for implantable systems.

What is claimed is:

1. A method for cardiac pacing, said method comprising directing vibrational pacing energy at one or more regions of the left ventricle, wherein the vibrational energy selectively stimulates the left ventricle, wherein the vibrational pacing energy is delivered as single or multiple bursts having a frequency from 20 kHz to 5 MHz, a pulse duration from 0.12 μsec to 13 msec, a duty cycle from 0.1% to 100%, and an intensity greater than 0.2 W/cm$^2$.

2. A method as in claim 1, further comprising delivering pacing energy to at least the right ventricle.

3. A method as in claim 2, wherein delivering pacing energy to the right ventricle comprises delivering vibrational pacing energy.

4. A method as in claim 2, wherein delivering pacing energy to the right ventricle comprises delivering electrical pacing energy.

5. A method as in claim 1, further comprising delivering pacing energy to at least the right atrium.

6. A method as in claim 5, wherein delivering pacing energy to the right atrium comprises delivering vibrational pacing energy.

7. A method as in claim 5, wherein delivering pacing energy to the right atrium comprises delivering electrical pacing energy.

8. A method as in any one of claims 2 and 5, further comprising synchronizing contraction of the left and right ventricles.

9. A method as in claim 8, wherein synchronizing comprises detection of an electrically paced beat and an immediate vibrationally paced beat response.

10. A method as in claim 8, wherein synchronizing comprises detection of a vibrationally paced beat and an immediate electrically paced beat response.

11. A method as in any one of the claims 1 to 4, 6, and 7 further comprising detecting the presence or absence of cardiac signals originating in the ventricles or atria of the heart and triggering or inhibiting electrical or vibrational energy based on programmed parameters.

* * * * *